US008663180B2

(12) United States Patent
Tanghoej et al.

(10) Patent No.: US 8,663,180 B2
(45) Date of Patent: Mar. 4, 2014

(54) IRRIGATION SYSTEM WITH A PUMP

(75) Inventors: Allan Tanghoej, Kokkedal (DK); Marlene Corydon Sinvani, Espergaerde (DK); Jesper Grøndahl Lund, Bagsvaerd (DK); Lars Olav Schertiger, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 1023 days.

(21) Appl. No.: 12/522,218

(22) PCT Filed: Jan. 21, 2008

(86) PCT No.: PCT/EP2008/050630
§ 371 (c)(1),
(2), (4) Date: Feb. 15, 2010

(87) PCT Pub. No.: WO2008/087220
PCT Pub. Date: Jul. 24, 2008

(65) Prior Publication Data
US 2010/0174252 A1  Jul. 8, 2010

Related U.S. Application Data

(60) Provisional application No. 60/881,164, filed on Jan. 19, 2007.

(30) Foreign Application Priority Data

Jan. 19, 2007  (EP) ................................ 07001124

(51) Int. Cl.
*A61F 5/44*  (2006.01)
(52) U.S. Cl.
USPC ................ 604/328; 604/27; 604/35; 604/48; 604/65; 604/118; 604/119; 604/317; 604/318; 604/322; 604/326; 137/205; 141/35; 141/59; 141/95; 141/198; 119/14.46

(58) Field of Classification Search
USPC .................................. 604/318, 322, 326, 328
See application file for complete search history.

(56) References Cited

U.S. PATENT DOCUMENTS

| 3,459,175 | A | 8/1969 | Miller |
| 3,766,920 | A | 10/1973 | Greene |
| 3,889,676 | A | 6/1975 | Greene |
| 3,990,448 | A | 11/1976 | Mather et al. |
| 4,385,631 | A | 5/1983 | Uthmann |
| 4,525,156 | A | 6/1985 | Benusa et al. |

(Continued)

FOREIGN PATENT DOCUMENTS

| BE | 370821 | A2 | 9/1994 |
| DE | 195412 | C | 5/1907 |

(Continued)

*Primary Examiner* — Tatyana Zalukaeva
*Assistant Examiner* — Ilya Treyger
(74) *Attorney, Agent, or Firm* — Coloplast Corp., Coloplast A/S; Nick Baumann

(57) ABSTRACT

An irrigation system comprising: a reservoir with an inlet for pouring liquid into the reservoir, the inlet defining a closing element for closing the inlet; an insertion member defining an insertion end for insertion into a body cavity a human being, the insertion member defining at least one opening; and a liquid tube fluidly connecting the reservoir and having with the insertion member. At least one of reservoir and the insertion member is permanently fastened to the liquid tube.

17 Claims, 9 Drawing Sheets

(56) References Cited

U.S. PATENT DOCUMENTS

| | | | |
|---|---|---|---|
| 4,755,168 A * | 7/1988 | Romanelli et al. | 604/34 |
| 4,874,363 A | 10/1989 | Abell | |
| 5,019,056 A | 5/1991 | Lee et al. | |
| 5,180,387 A | 1/1993 | Ghajar et al. | |
| 5,197,950 A | 3/1993 | Clayton | |
| 5,250,024 A | 10/1993 | Kensey | |
| 5,259,383 A * | 11/1993 | Holstein et al. | 600/437 |
| 5,300,022 A | 4/1994 | Klapper et al. | |
| 5,330,447 A | 7/1994 | Barth | |
| 5,405,319 A | 4/1995 | Abell et al. | |
| 5,499,970 A | 3/1996 | Olson | |
| 5,643,228 A | 7/1997 | Schucart et al. | |
| 5,683,640 A | 11/1997 | Miller et al. | |
| 5,800,409 A | 9/1998 | Bruce | |
| 5,810,202 A | 9/1998 | Hoback et al. | |
| 5,833,658 A | 11/1998 | Levy et al. | |
| 5,976,103 A | 11/1999 | Martin | |
| 6,096,007 A | 8/2000 | Haan et al. | |
| 6,106,506 A | 8/2000 | Abell et al. | |
| 6,264,636 B1 | 7/2001 | Holm et al. | |
| 6,533,763 B1 | 3/2003 | Schneiter | |
| 6,918,898 B2 | 7/2005 | King | |
| 7,270,647 B2 * | 9/2007 | Karpowicz et al. | 604/35 |
| 8,001,984 B2 * | 8/2011 | Sasaki | 134/95.2 |
| 2004/0039348 A1 * | 2/2004 | Kim et al. | 604/264 |
| 2005/0148954 A1 | 7/2005 | Abell | |
| 2006/0009732 A1 | 1/2006 | Hardy | |
| 2007/0010798 A1 * | 1/2007 | Stoller et al. | 604/544 |
| 2008/0243054 A1 * | 10/2008 | Mollstam et al. | 604/31 |

FOREIGN PATENT DOCUMENTS

| | | |
|---|---|---|
| DE | 19536118 A1 | 4/1996 |
| EP | 0109897 A1 | 5/1984 |
| EP | 0381062 A2 | 8/1990 |
| FR | 1222961 A1 | 6/1960 |
| FR | 1460776 A1 | 1/1966 |
| GB | 2224212 A | 5/1990 |
| HU | 191765 B | 4/1987 |
| HU | P9903396 A2 | 2/2000 |
| JP | 31-8190 | 5/1956 |
| JP | 40-17488 | 6/1965 |
| JP | 55-145094 | 11/1980 |
| JP | 2000-501309 | 2/2000 |
| WO | WO/95/28138 | 10/1995 |
| WO | WO/96/25188 | 8/1996 |
| WO | WO 98/23312 * | 11/1996 |
| WO | 97/20583 | 6/1997 |
| WO | WO/98/23312 | 6/1998 |
| WO | WO/98/30270 | 7/1998 |
| WO | WO/99/30652 | 6/1999 |
| WO | WO/99/59656 | 11/1999 |
| WO | WO/00/40182 | 7/2000 |
| WO | WO/2004/006993 | 1/2004 |
| WO | WO/2005/003267 | 1/2005 |
| WO | WO/2005/032617 | 4/2005 |
| WO | WO2005/048890 | 6/2005 |
| WO | WO 2004/006993 * | 4/2006 |

* cited by examiner

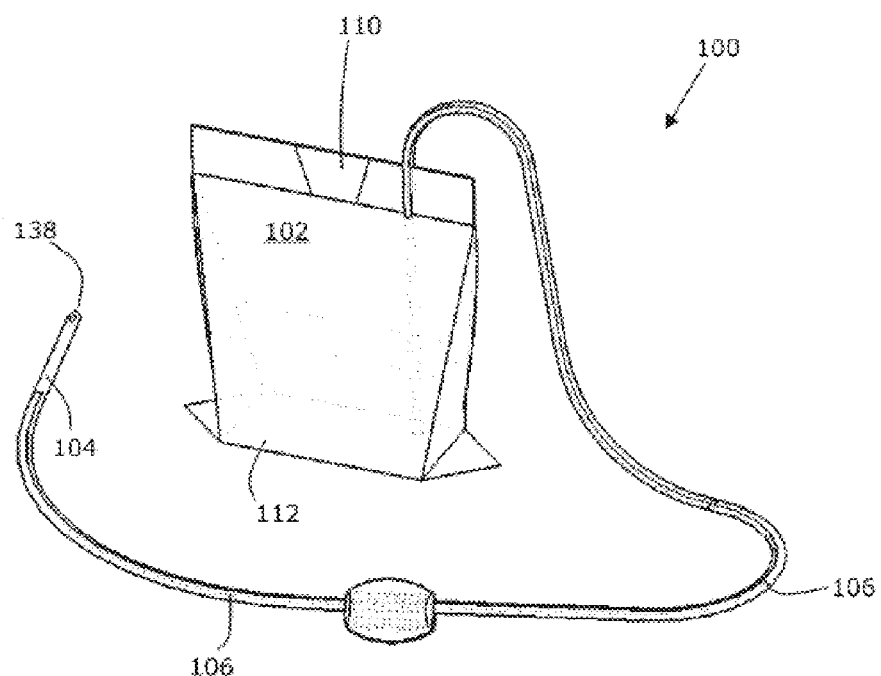
Fig. 5
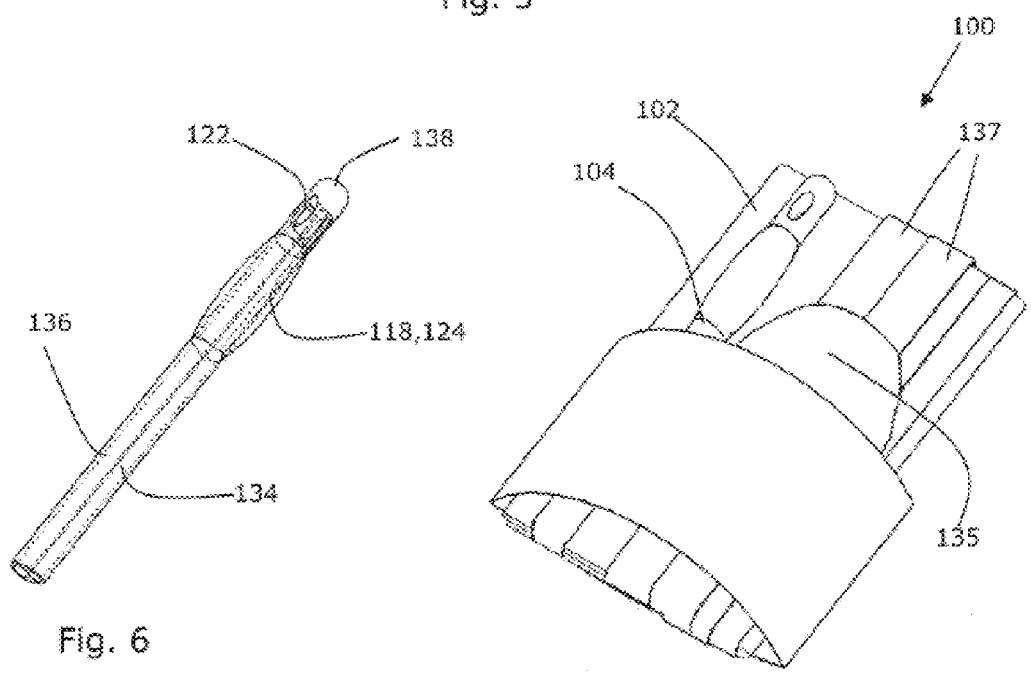
Fig. 6
Fig. 7

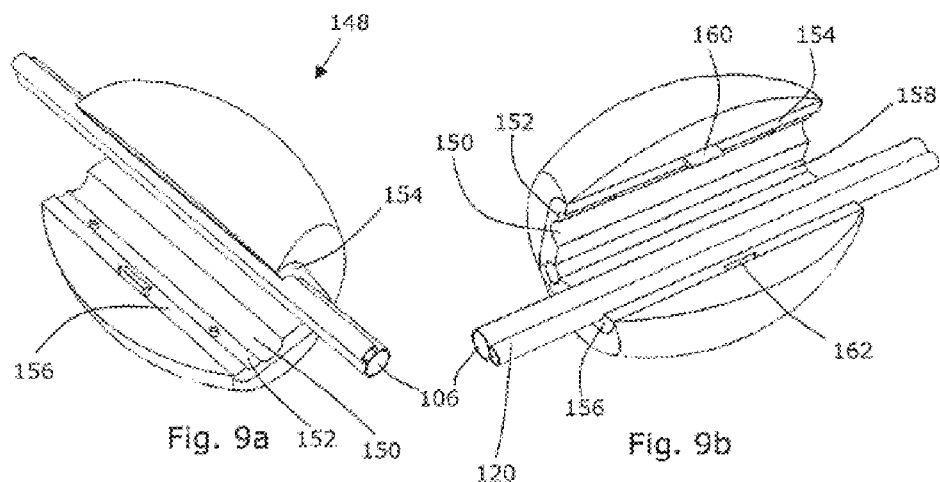
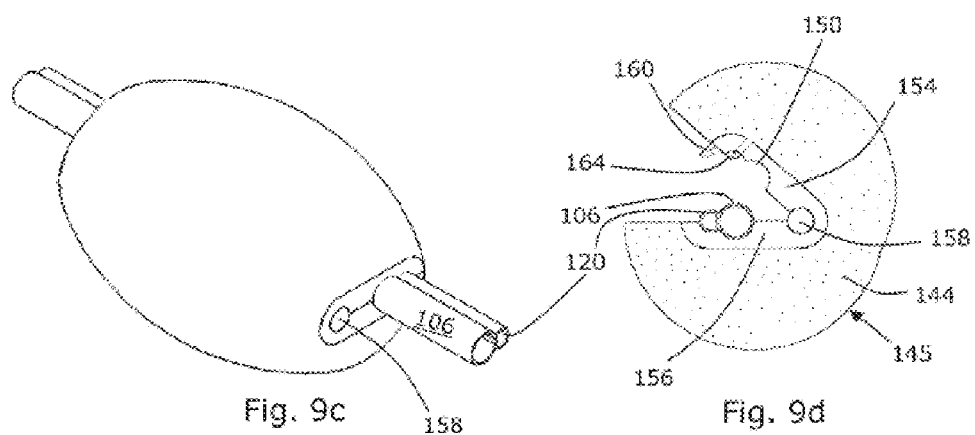
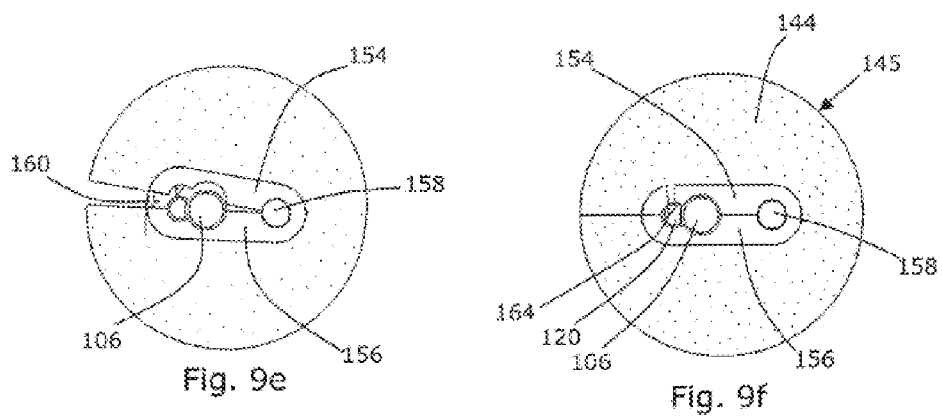

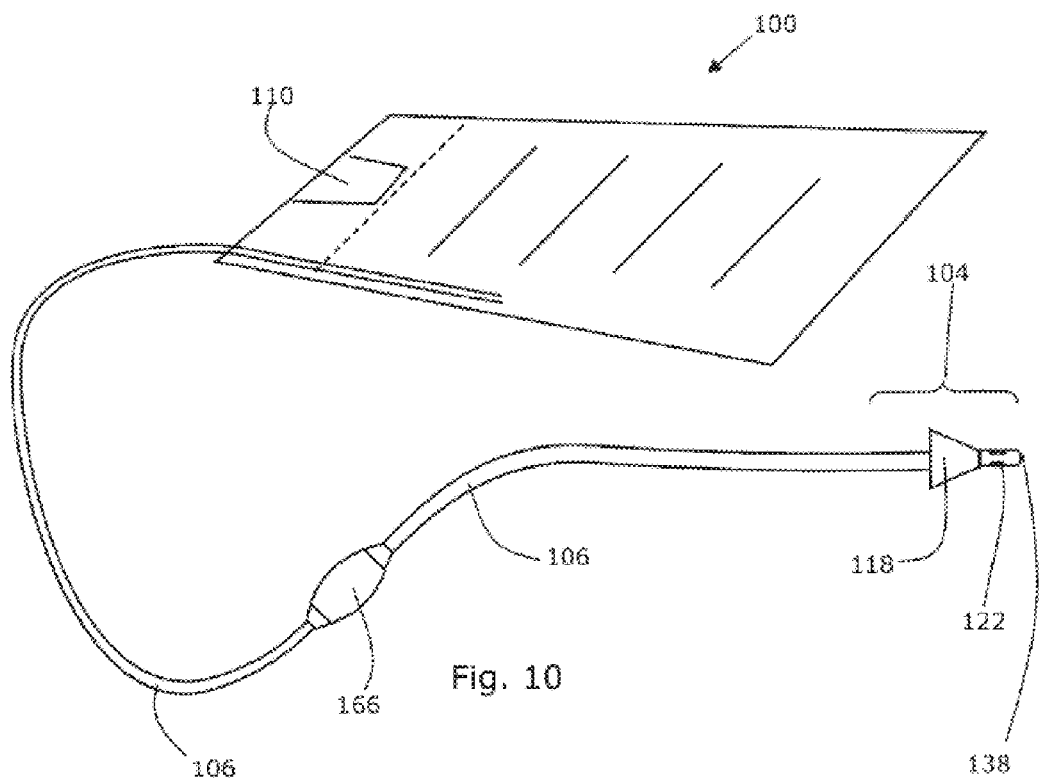
Fig. 10
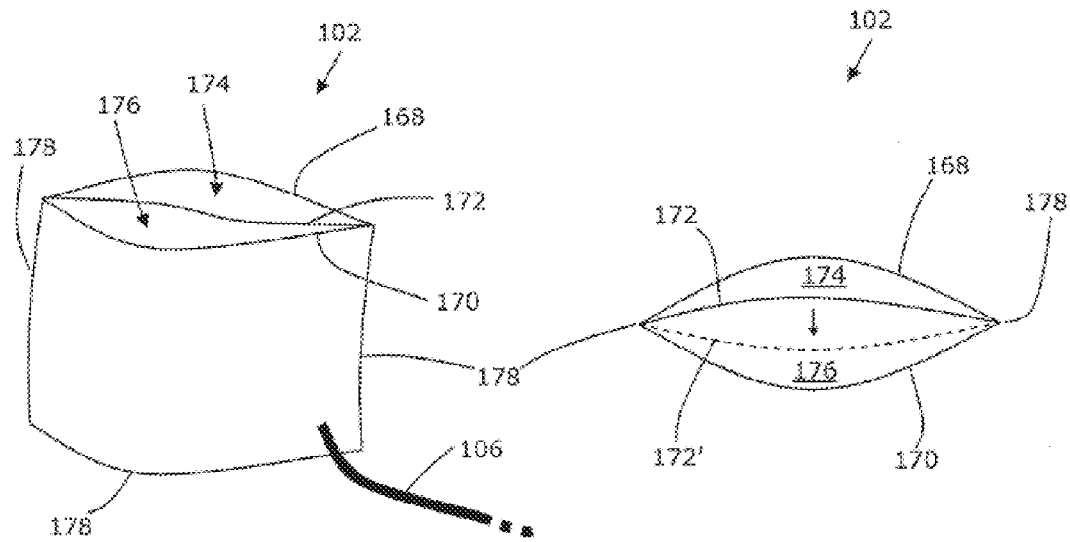
Fig. 11a
Fig. 11b

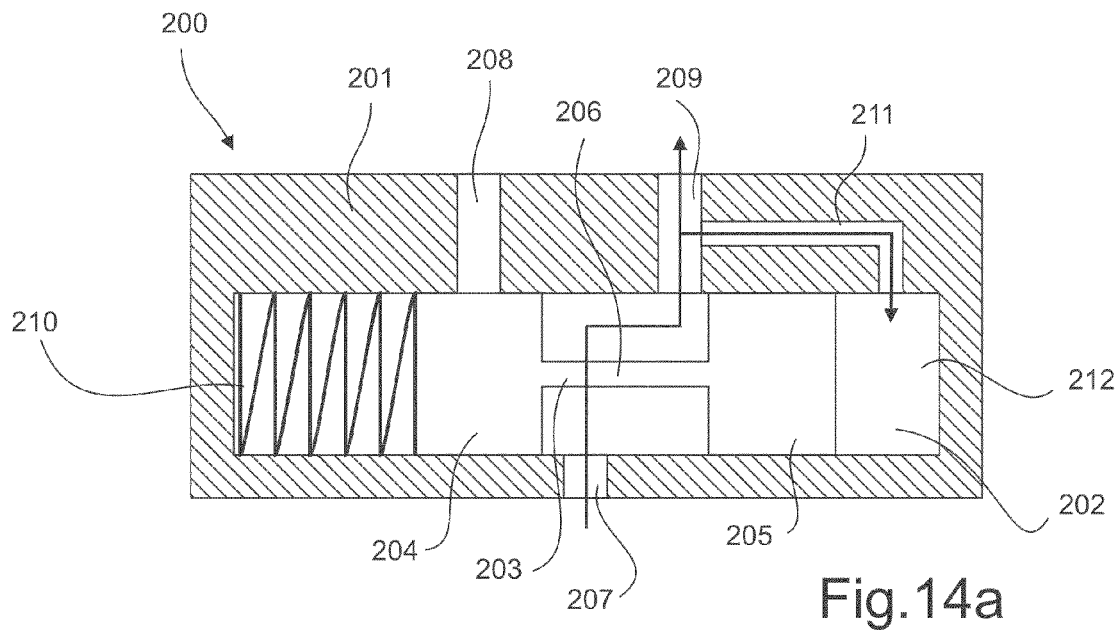
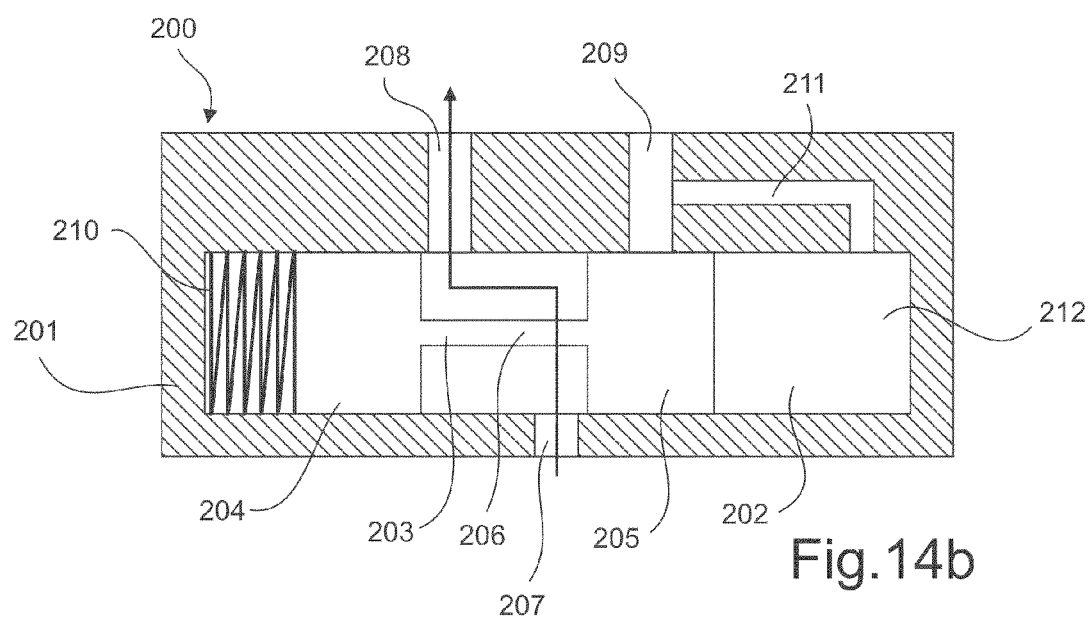

IRRIGATION SYSTEM WITH A PUMP

CROSS REFERENCE TO RELATED APPLICATIONS

This application is a nationalization of PCT/EP2008/050630 filed Jan. 21, 2008.

BACKGROUND OF THE INVENTION

1. Field of the Invention

The present invention relates to an irrigation system with a reservoir fluidly connected to an insertion member for insertion into a body cavity of a human being, and a pump for pumping liquid contained in the reservoir out through an outlet of the insertion member and into the body cavity. Furthermore, the present invention relates to a method of performing an irrigation on a human body by use of the irrigation system and a method of manufacturing the irrigation system.

2. Description of the Prior Art

An irrigation system may for certain users be used on a daily basis, depending of the user's need. This is for example the case for people suffering from spinal cord injuries, spinal bifida or multiple sclerosis. The system is used to improve quality of life by preventing constipation, reducing time spent for bowel emptying procedures and increasing independency.

Various systems are known in the art.

A simple system widely used, e.g. at hospitals, constitutes a bag that is elevated above the person to have the trans anal irrigation. The bag is via a tube connected to a catheter, which is inserted through the anus into the rectum. The liquid in the bag is inserted into the person due to the difference of height between the person and the bag, causing a pressure difference. A drawback of this very simple system is that in order to make the system work the bag must be elevated to a position above the person in order to obtain the wanted pressure difference.

A system that overcomes this problem is disclosed in US2005/0148954A1. The apparatus disclosed in US2005/0148954A1 is designed to provide a colonic lavage with the capability of providing manually controlled pulsation to the lavage liquid or medicaments through the use of a manual pump. The apparatus comprises a speculum that is configured and sized to be inserted into the patient's rectum. A delivery line is secured to an inlet of the speculum. The delivery line is secured to the inlet of the speculum. The manual pump is disposed in-line with the delivery line and connected to the second section. A male connector and female connector interconnect the delivery line with the lavage liquid reservoir. A first valve is operably connected to the delivery line and allows liquid to flow from the lavage liquid reservoir to the speculum. Also an alternative valve construction is disclosed where the manual pump operates a valve inline with the delivery line such that operating the manual pump opens and closes the valve, thereby pulsating the lavage liquid into the colon of the patient. The apparatus further comprises a drain line connected to the speculum at an outlet. The drain line is in flow communication with a mouth of the speculum, so as to allow liquids and material washed from the colon to be drained through the speculum.

Even though this invention overcomes the need of positioning the bag in an elevated position, this is a rather complex system that facilitates both the insertion of the lavage liquid into the person as well as draining of thereof, and it requires a lot of operations to be performed.

Other systems are disclosed in US2006/0009732. One of the systems is designed to provide a colonic lavage with the capability of providing manually controlled pulsation to the lavage liquid through a manual pump. The manual pump can be a conventional in-line squeeze bulb. In an embodiment, a check valve can be disposed in-line with the supply conduit or the manual pump.

SUMMARY OF THE INVENTION

It is an object of an embodiment of the present invention to provide a simple system that is easy to use. Moreover, it is an object of an embodiment of the present invention to provide a system wherein the elements of the system are not accidentally disconnected during use.

Furthermore, it is an object of an embodiment of the present invention to provide a system, which is ready-to-use for the patient so as to reduce the time spent with the irrigation as its parts need not be assembled by the user. Moreover, it is an object of an embodiment of the present invention to provide an irrigation system, which may be provided to the user in a compact configuration.

Additionally, it is an object of an embodiment of the invention to provide a system, which may be disposed after irrigation whereby the user need not clean the system upon use. Moreover, it is an object of an embodiment of the invention to provide a system, which is discrete, compared to known systems.

BRIEF DESCRIPTION OF THE INVENTION

In a FIRST aspect, the present invention relates to an irrigation system for irrigation of a body cavity, the system comprising:
- a reservoir with an inlet for pouring liquid into the reservoir, the inlet defining a closing means for closing the inlet;
- an insertion member defining an insertion end for insertion into a body cavity through a body opening of a human being, the insertion member defining at least one opening; and
- a liquid tube (i.e. a tube for holding and/or conducting liquids) fluidly connecting the reservoir with the insertion member;

wherein at least one of reservoir and the insertion member is permanently fastened to the liquid tube.

In the context of the present invention the term "permanently fastened to" shall be understood as two elements fixed to each other such that a fluid tight seam or seal is defined between the two elements e.g. a welding seam, a gluing seam or a sealing gasket. If the two elements are removed from each other, the system is irreversibly ruptured and said two elements cannot be reattached to each other by hand and without use of tools. In some embodiments the seam between the two elements is sufficiently strong to ensure that if the two elements are pulled away from each other, the probability of the seam breaking is smaller than or equal to the probability of one of the elements is breaking.

The system may be used for irrigation performed to any body cavity such as the uterus, the bowel (the intestinal system) and the bladder.

In the context of the present invention the term "intestinal irrigation" shall be understood as any irrigation/cleaning, by means of a liquid of any part of the digestive/bowel system between the stomach and the anus. Accordingly, intestinal irrigation comprises irrigation in the rectum, the appendix, the colon and the small intestine i.e. ileum, jejunum and duodenum. In most embodiments the system is inserted through the exit of the intestinal system of the user such as a natural anus or artificial anus (a stoma). When inserted through said exit, an irrigation liquid may be expelled in an upstream direction of the intestinal system relative to the exit, by means of the insertion member.

As the user of the present invention need not assembly the elements of the intestinal irrigation system, the risk of wrongly assembling the system is eliminated. As most users only carry a limited number of devices and often only a single device, wrong assembly is highly unwanted as such wrong assemblies may cause the system to be damaged whereby the user may be left without any means of bowel emptying equipment. Furthermore, wrong assembly, may lead to spillage of faecal matter on the floor of the toilet. Moreover, the preassembled system is easier and faster for the user to use compared to conventional systems. Furthermore, the system will be appreciated by users with no, insufficient or poor dexterity. A simplified system/procedure may very well increase the independency of the user as it reduces or totally avoids the need for assistance from others during the irrigation procedure.

The reservoir may be made in one piece or by joining one or more pieces such as plastic foils/films together e.g. by gluing or welding. In one embodiment at least a part of the reservoir is transparent, such that the user can visually determine whether a liquid is present in the reservoir. In another embodiment, the entire reservoir is transparent. The reservoir may comprise means for indicating the volume of a liquid contained in the reservoir such as indications on a sidewall of the reservoir.

The inlet may be adapted to allow at least a part of a water tap to be inserted into the inlet whereby water running from the water tap may flow into the reservoir without spillage. The inlet may comprise means for temporarily fastening the inlet/reservoir to the water tap in a position wherein water running from the tap fills the reservoir. This allows a user to fill the reservoir by use of one hand i.e. by attaching the reservoir to the water tap by means of a first hand, and subsequently opening a valve of the tap by means of the same first hand whereby water is allowed to run into the reservoir.

The closing means may be a non-return valve allowing liquid to enter the reservoir through the inlet while preventing the liquid from escaping the reservoir through the inlet. Alternatively, or as a supplement, the closing means may comprise a clamp or a screw cap which when fastened to the inlet prevents liquid from flowing into and out of the reservoir through the inlet.

A proximal insertion end of the insertion member may define a smooth surface so as to adapt the insertion member to be inserted into a body cavity of a human being e.g. through the anus of the human being.

The insertion member defines at least one opening such as two, three, four or five. The at least one opening is arranged such with respect to the proximal end of the insertion member that when the insertion member is at least partly inserted (e.g. through the artificial/natural anus), the opening(s) is/are positioned in the body cavity, whereby a liquid expelled through the at least one opening is received in said body cavity.

The reservoir and the insertion member are fluidly connected by a liquid tube, which may be transparent. The tube may comprise a thermoplast such as PVC/PP/PE or a thermoplastic elastomer like a Styrol-Block-Copolymere such as a PUR or a SEBS compound or a cross-linked elastomer like silicone or latex. In one embodiment the liquid tube takes the form of a foil tube. The sidewalls of the foil tube are movable towards and into contact with each other allowing a flat and compact configuration. This is desirable prior to use and after use when the user disposes the system. In the context of the present invention, the term "tube" shall be understood as a conduit defined by of a long hollow object (e.g. cylindrical) used to hold and conduct liquids or gases.

Moreover, at least one of the reservoir and the insertion member is permanently fastened to the liquid tube. In one embodiment the reservoir is permanently fastened to the liquid tube. In another embodiment the insertion member is permanently fastened to the liquid tube and in a third embodiment both the reservoir and the insertion member are permanently fastened to the liquid tube.

The reservoir, the liquid tube and/or the insertion member may comprise a non-return valve for preventing upstream flow of liquid from the at least one opening and towards the reservoir. This prevents contamination of the system e.g. by faecal matter or blood present in the body cavity during use.

In one embodiment, where the non-return valve is arranged at the end of the liquid tube, the non-return valve may additionally or alternatively also be biased so that a certain amount of pressure has to be built in the liquid tube before the irrigation liquid can flow out. This prevents irrigation liquid from unintentionally dripping from the liquid tube.

In one embodiment the system comprises a pump for pumping liquid contained in the reservoir out through the at least one opening of the insertion member via the liquid tube. In one embodiment the pump comprises a manual pump adapted to be operated manually by hand or foot or arm or mouth. The manual pump may take the form of a foil pump with a resilient element. Upon compression of the resilient element a fluid such as liquid or gas, contained in the pump is expelled from the pump and upon removal of the force used to compress the resilient element, the element will return to its non-biased state. The resilient material may be a shape-memory material such as a spring or an open-celled foam. The resilient material may be accommodated in a foil such as a plastic foil/film. The use of a foil pump makes it easier for the user to carry the system as such pumps are light weighted compared to conventional rubber pumps. Moreover, the pump may on delivery to the user be provided in its compacted state in order to increase the overall compactness of the system.

In another embodiment, the pump comprises an electrical pump, such as an electric air/gas pump. Use of an electrical pump is advantageous for patients with poor dexterity. The electrical pump may be adapted to be separated from the system so to allow it to be reused and to allow the user to dispose the reservoir, the liquid tube and the insertion member.

In one embodiment the electrical pump comprises a control unit for controlling the liquid/gas flow in the system. The electrical pump may comprise a rechargeable battery, which may be adapted to be recharged by being connected to a power supply such as mains or by means of a manually operable generator, e.g. comprising a crank. By turning the crank the user may recharge the battery. In order to allow a person with reduced dexterity of one of the hands/arms, to operate the generator, the generator may comprise means for temporarily fastening the generator to a third element such as a chair, thus allowing the user to rotate the crank with the hand/arm having sufficient dexterity. By providing a rechargeable battery the user is not dependent on a power supply. This increases the freedom and the independency of the user as most public toilets does not provide access to a power supply. Accordingly, the user may recharge the battery e.g. by means of the generator in a place different from the place of irrigation which makes the actual irrigation process faster, more discrete and less complicated.

In one embodiment the pump—manual or electrical—is a peristaltic pump into which the liquid tube may be inserted so as to allow the pump to pump liquid through the tube without contacting the liquid. This prevents contamination of the liquid by the pump and vice versa. Moreover, the peristaltic pump enables the user to position the pump at any desired position along the liquid tube, thus, increasing the freedom of the user.

In one embodiment the pump is a liquid pump (i.e. a pump for pumping liquids) with a pump inlet and a pump outlet, the pump inlet and pump outlet being permanently fastened to the tube, such that operation of the pump causes a liquid contained in the reservoir to flow out through the at least one opening of the insertion member. The liquid pump may comprise a non-return valve arranged to prevent liquid from flowing upstream from the pump towards the reservoir.

In one embodiment the pump is an electrical water pump comprising a control unit for controlling the liquid flow in the system. As an example the control unit may be adapted to change the flow rate of the liquid in the liquid tube in a predetermined sequence. The control unit may operate the sequence once or repeatedly e.g. a predetermined number of times. In one embodiment the flow rate is varied over time in a predetermined sequence in order to stimulate the irrigation process.

In one embodiment, the pump is a gas pump (i.e. a pump for pumping gas) arranged such with respect to the reservoir that upon activation of the pump, gas pressure in the reservoir increases whereby a liquid contained in the reservoir is displaced (flows) into the liquid tube and out through the at least one opening. It will be appreciated that in order to achieve said effect, the liquid tube must be arranged such with respect to the reservoir that for most liquid levels, the liquid covers an outlet of the reservoir and/or the inlet of the liquid tube. In many embodiments the outlet/inlet is positioned in a bottom part of the reservoir. Moreover, in order to enable the reservoir to be inflated and to force liquid into the liquid tube, the inlet used to fill liquid into the reservoir must be closable so as to enable the reservoir to be inflated without air escaping through the inlet.

The gas pump may form an integral part of the reservoir e.g. by providing the reservoir in the form of two pieces of foil sealed together and by integrating one of the above mentioned foil pumps into the reservoir. The latter solution is easy to manufacture, easy to provide to the user in a compact configuration and easy to use. Alternatively, the system may comprise a gas tube fluidly interconnecting the gas pump and the reservoir. The gas tube may be a foil tube, which may be permanently fastened to the gas pump and/or the reservoir.

In order to prevent that the insertion member slips out of the body cavity during irrigation, the insertion member may comprise a retaining means for retaining the insertion member in the body cavity when inserted through the body opening. The retaining means may be changeable between two configurations a non-retaining configuration allowing the insertion member to be inserted into and retracted from the body opening, and a retaining configuration wherein the retaining means prevents retraction of the insertion member when it is inserted into the body cavity through the body opening.

In order to provide a retaining means, which is adapted to define the two positions, the retaining means may comprise a balloon fluidly connected with a balloon pump such that operation of the balloon pump causes the balloon to expand. The balloon may be a gas balloon or a liquid balloon. The gas/liquid pump may be a foil pump as described in the aforementioned. The retaining means may be defined on an outer surface of the insertion end.

In order to reduce the number of pumps in the irrigation system, the system may comprise an switchable pump defining both the balloon pump and the gas pump. In order to allow the user to change between inflation of the balloon and inflation of the reservoir, the switchable pump comprises a switch defining a first position in which the switchable pump is fluidly connected to the gas balloon and a second position in which the switchable pump is fluidly connected to the reservoir. Thus during use, the user may position the switch in the first position so as to inflate the balloon, and subsequently position the switch in the second position in order to inflate the reservoir so as to displace liquid contained in the reservoir into the liquid tube and further into the body cavity.

In one embodiment the reservoir is divided into two chambers—a liquid chamber and a gas chamber. This may be done by means of a membrane at least a part of which is movable between a first position and a second position such that the volume of the gas chamber is smaller when the membrane is positioned in the first position than when it is positioned in the second position. When the gas chamber is pressurised, said chamber expands causing the membrane to be moved towards the second position whereby the volume of the liquid chamber decreases and any fluid contained therein is displaced into the liquid tube. An advantage of the two-chamber system is that gas used to displace the liquid from the reservoir into the liquid tube is prevented from creating air pockets in the liquid tube.

In one embodiment, the gas pump is fluidly connected to the balloon and comprises an over-pressure valve arranged and designed such that when the pressure in the balloon reaches a predetermined pressure level, the over-pressure valve guides air into the reservoir whereby the reservoir is inflated and a liquid provided in the reservoir is displaced into the liquid tube. An advantage of the latter embodiment is, that only one pump need to be provided and that a switch for switching between the balloon tube and the gas tube is superfluous.

In one embodiment the inserting member is provided with a hydrophilic coating in order to create a slippery surface thereon (prior to insertion) by swelling of the coating. In a further embodiment at least a part of (such as all of) the inserting member is located within the reservoir on delivery. Thus when the user fills water into the reservoir, the hydrophilic coating is subjected to said water whereby the swelling process is initiated. In the latter embodiment, the reservoir may be subdivided into several fluidly connected chambers one of which may be positioned such that for most levels of water, the hydrophilic coating is subjected to the liquid.

Moreover, the reservoir may be adapted to allow removal of the inserting member from the reservoir without creating a passage for drainage of the reservoir. Accordingly, in one embodiment the reservoir comprises a swelling compartment adapted to allow the outer surface of the inserting member to be subjected to a swelling medium (a liquid) and a compression compartment adapted to be pressurised so as to allow liquid contained in the compartment to be displaced into the liquid tube. In another embodiment the swelling compartment and the compression compartment are identical. In the former embodiment, removal of the inserting end may cause a passage between the two compartments to be closed whereby pressurisation of the compressing compartment causes the liquid contained in said compartment to be displaced into the liquid tube and not into the swelling compartment. However when the inserting end is provided in the swelling compartment, the two compartments are fluidly connected via the passage thus allowing liquid filled into the compression compartment to flow into the swelling compartment. When the compression compartment and the swelling compartment are identical, the aforementioned passage is not defined.

Thus during use, the user may fill water into the reservoir, whereby the swelling and compression compartments are filled with water. When the inserting end has been subjected to the liquid (the swelling medium) for a period of time such as 30 sec, sufficient to ensure swelling of the hydrophilic coating, the inserting end is removed from the swelling compartment. Upon removal, the passage between the swelling compartment and the compression compartment is automatically closed, and the user may pressurise the compression compartment in order to displace the liquid into the liquid tube. It will be appreciated that in some embodiments, the passage may be adapted to be closed manually by the user, before or after removal of the inserting end from the swelling compartment.

In a further embodiment the inlet of the reservoir defines a first passage connected to the swelling compartment and second passage connected the compression compartment. When water is filled into the inlet, the water will flow into both compartments via the first and second passages. Moreover the reservoir may be designed such that when the inlet is closed, the swelling compartment and the compression compartment are not fluidly connected whereby pressurisation of the compression compartment does not lead to displacement of the water into the swelling compartment, not even when the inserting end has been removed from the swelling compartment.

In one embodiment, the reservoir defines only one compartment which is used both as a compression compartment and a swelling compartment. In the latter embodiment, the inserting member may be inserted through the inlet of the reservoir such that a liquid filled into the reservoir causes the inserting member to be subjected to a swelling medium (the liquid).

In one embodiment at least one of the pumps defines one or more means for temporarily fixing the fingers of the user to an outer surface of the pump. Accordingly, when the fingers are temporarily fixed to the outer surface and the user moves the fingers away from each other, the compartment of the pump expands thus allowing air/water to be sucked into the compartment. Moreover when the fingers are moved towards each other, the compartment is compressed whereby air/water contained in the compartment may be displaced into a tube such as the gas tube, the balloon tube or the liquid tube. In one embodiment said means for fixing the fingers to the outer surface forms part of a glove, which also defines the compartment of the pump. Thus in order to use the pump, the user inserts the hand into the glove and moved the fingers away from and towards each other. It will be appreciated that the pump may comprise one or more non-return valves as is described in the aforementioned. When the pump forms a glove, at least a part of the walls of the pump may contact the palm of the user during use.

In one embodiment the glove pump comprises an elastic material forcing the pump into its compressed state and thus in order to perform the pumping action, the user must force his fingers away from each other in order to increase the volume of the compartments, and release the finger pressure in order to contract the compartment.

When the pump comprises means for temporarily fixing the fingers to the outer surface of the compartment, the pump may not need to comprise resilient element for forcing the walls away from each other (as is described in the aforementioned), as the walls during use are moved away from each other by the user. This allows an extremely compact configuration of the pump, and thereby the irrigation device.

In a SECOND aspect the present invention relates to a method of performing an irrigation of a body cavity of a human being by use of an irrigation system according to the first aspect of the invention, the method comprising the steps of:
  filling a liquid into the reservoir via the liquid inlet;
  inserting the insertion member into a body cavity via a body opening of a human being;
  operating the pump so as to pump at least a part of the liquid from the reservoir into the body cavity;
  retracting the insertion member from the body cavity; and
  disposing the system.

In one embodiment the body cavity is the intestinal system (bowel) of a human being.

In one embodiment the abovementioned steps are performed in the above order, while in other embodiments the order may be different e.g. the insertion member may be inserted prior to filling liquid in the reservoir. The liquid filled in the reservoir may be water. The step of filling may comprise the step of closing the inlet. Moreover, the method may comprise the step of emptying the reservoir.

In one embodiment the reservoir is a foil bag with a leaf which when removed allows the user to empty the reservoir. Moreover, the step of emptying the reservoir may further comprise the steps of:
  removing the leaf so as to create an emptying outlet, and
  emptying the reservoir by allowing the remaining liquid to flow out through the emptying outlet.

In a further embodiment the method comprises the step of:
  inflating the retaining means so as to retain the inserting member in the body cavity and prevent the inserting member from slipping out of the body opening, and/or
  deflating the retaining means so as to allow the inserting member to be retracted from the body cavity.

The invention according to the second aspect may comprise any combination of feature(s) and/or element(s) of the first aspect of the invention.

In a THIRD aspect the present invention relates to a method of manufacturing an irrigation system according to the first aspect of the invention, comprising at least one of the steps of:
  permanently fastening the liquid tube to the reservoir;
  permanently fastening the liquid tube to the insertion member;
  permanently fastening the liquid tube to the inlet of the liquid pump;
  permanently fastening the liquid tube to the outlet of the liquid pump;
  permanently fastening the gas tube to the reservoir;
  permanently fastening the gas tube to the gas pump;
  permanently fastening the balloon to an outer surface of the insertion member;
  permanently fastening the balloon tube to the balloon;
  permanently fastening the balloon tube to the balloon pump;
  permanently fastening the switchable pump to at least one of the gas tube and the balloon tube; and
  permanently fastening the membrane for dividing the reservoir into a gas chamber and a liquid chamber to the walls of the reservoir.

At least one of the steps of permanently fastening may comprise the step of:
  permanently fastening by welding, or
  permanently fastening by gluing.

The invention according to the third aspect may comprise any combination of feature(s) and/or element(s) of the first aspect of the invention.

BRIEF DESCRIPTION OF THE DRAWINGS

The invention is now described with reference to the drawings in which.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
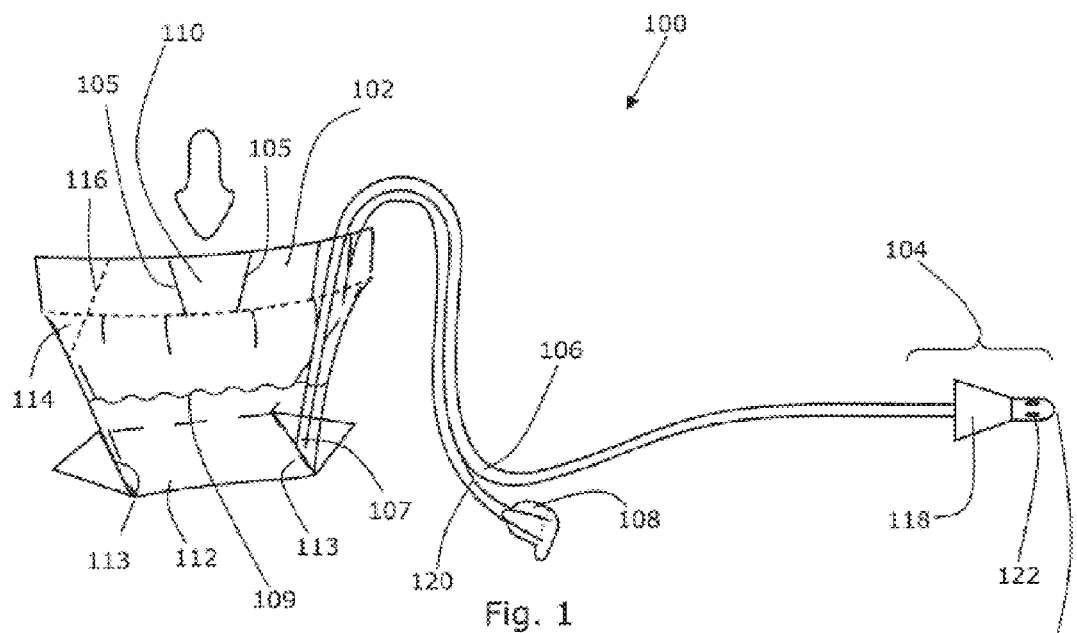
FIG. 1 discloses a first embodiment of the disposable irrigation system having a cone-shaped retaining element, FIG. 2 discloses second embodiment of the disposable irrigation system wherein the retaining element is defined by a balloon catheter, FIG. 3 discloses a third embodiment of the disposable irrigation system wherein the pump is provided as a pump with a switch, FIG. 4 discloses a fourth embodiment of a disposable irrigation system wherein the fluid pump and the balloon pump are joined into one single unit, FIG. 5 discloses a fifth embodiment of the disposable irrigation system wherein the pump is integrated into the liquid tube, FIG. 6 discloses an embodiment of the insertion member, FIG. 7 discloses the irrigation system in the compacted state in which it is delivered to the user, FIGS. 8a and 8b disclose an embodiment of the foil pump, FIGS. 9a-f disclose an embodiment of an individually positionable pump, FIG. 10 discloses a sixth embodiment of the disposable irrigation system having a cone-shaped retaining element and an inline pump which is integrated into the liquid tube, FIGS. 11a and 11b disclose an irrigation system divided into a gas chamber and a liquid chamber, FIG. 12 discloses an irrigation system wherein the inserting member on delivery is provided in the reservoir ready for swelling, and FIG. 13 discloses an irrigation system with an over-pressure valve for guiding air into the reservoir, FIGS. 14a and 14b discloses an automatic valve for use in the irrigation system, and FIG. 15 discloses an embodiment of an irrigation system.

FIG. 1 discloses a disposable intestinal irrigation system 100 comprising a reservoir 102, an insertion member 104, a liquid tube 106 and a gas pump 108. The reservoir 102 is made by joining two sheets of foil together e.g. by welding or gluing. The foil may comprise a thermoplastic elastomer like Styrol-Block-Copolymere such as SEBS or PUR or a thermoplast like Polypropylen (PP), PE and PVC.

The reservoir 102 is adapted to contain a liquid such as a water-based liquid, which may be poured into the reservoir through the inlet 110 (reference number 108 indicates a water/liquid level). The inlet 110 defines a closing means (not shown) in the form of a non-return valve preventing liquid from exiting the reservoir 102 through the inlet 110. The inlet may define inclined surfaces 105 adapted to guide the liquid into the reservoir 102. In one embodiment the inlet 110 defines cross-sectional area of at least 3 cm$^2$ for at least one relative position of the sidewalls of the inlet.

The reservoir 102 may be adapted to withstand a pressure of at least 100 mbar, such as between 100 and 300 mbar, such as 150-250 mbar, such as 200 mbar. In one embodiment the reservoir 102 is adapted to rupture if the pressure inside it exceeds a predetermined pressure level such as a pressure level, which is uncomfortable inside the body cavity of a user.

In FIG. 1, the reservoir 102 is provided as a self-standing bag having a square bottom 112 e.g. made by two welds 113. By self-standing is meant that when the reservoir is partly filled it may stand unsupported on a surface such as a floor or in a sink. The reservoir further defines a leaf 114 adapted to be thorn off subsequent to irrigation, so as to allow the user to empty the reservoir after irrigation. The leaf 114 defines a tear line 116 e.g. made by a weld, providing a weakened zone which extent from one side of the reservoir to the top of the reservoir 102. It will be appreciated that the reservoir 102 may comprise any other means suitable for emptying the reservoir 102, such as an openable valve.

In order to allow the user to determine the volume of a liquid present in the reservoir, the reservoir 102 may comprise a volume scale (not shown) e.g. printed on the outer surface of the reservoir.

In the embodiment of FIG. 1, the liquid tube 106 is permanently fastened to the reservoir 102 and may be provided in the form of a flat tube such as a foil tube. The liquid tube may comprise a thermoplast such as PVC/PP/PE or a thermoplastic elastomer like a Styrol-Block-Copolymere such as a PUR or a SEBS compound or a cross-linked elastomer like silicone or latex. Moreover, the liquid tube 106 may be permanently fastened to the insertion member 104 so as to provide a fluid connection between the reservoir 102 and the insertion member 104. In one embodiment the insertion member 104 is provided as an extension of the liquid tube 106.

The insertion member 104 which may be stiffer than the liquid tube 106, may be coated with gel adapted to ease insertion of the insertion member. Alternatively, the outer surface of the insertion member 104 may comprise a hydrophilic material, which when subjected to a liquid such as water for a predetermined period of time such as 30 sec, causes the surface to be smoother than prior to subjection to the liquid.

In the embodiment of FIG. 1, the insertion member 104 defines a cone-shaped retaining means 118 which may comprise a material such as paper, carton, termoplast or an elastomer.

In order to inflate the reservoir 102, the irrigation system 100 comprises a gas pump 108, which is connected to the reservoir 102 via a gas tube 120. Upon operation of the gas pump the reservoir 102 is inflated whereby a liquid contained in the reservoir is displaced into the liquid tube 106 and out through an opening 122 of the insertion member 104. In order to prevent the inflated reservoir from deflating through the inlet (not shown) of the gas pump 108, the gas pump 108 may comprise a non-return valve (not shown) allowing air to be sucked into the gas pump 108 while preventing air from escaping the pump through the inlet. In one embodiment the gas pump 108 is a foil pump as described in relation to FIGS. 8a and 8b. It will be appreciated that in order to ensure that a liquid contained in the reservoir is displaced into the liquid tube 106, the tube inlet 107, must be arranged such that for most water levels, the inlet is covered by water.

Figure 2:
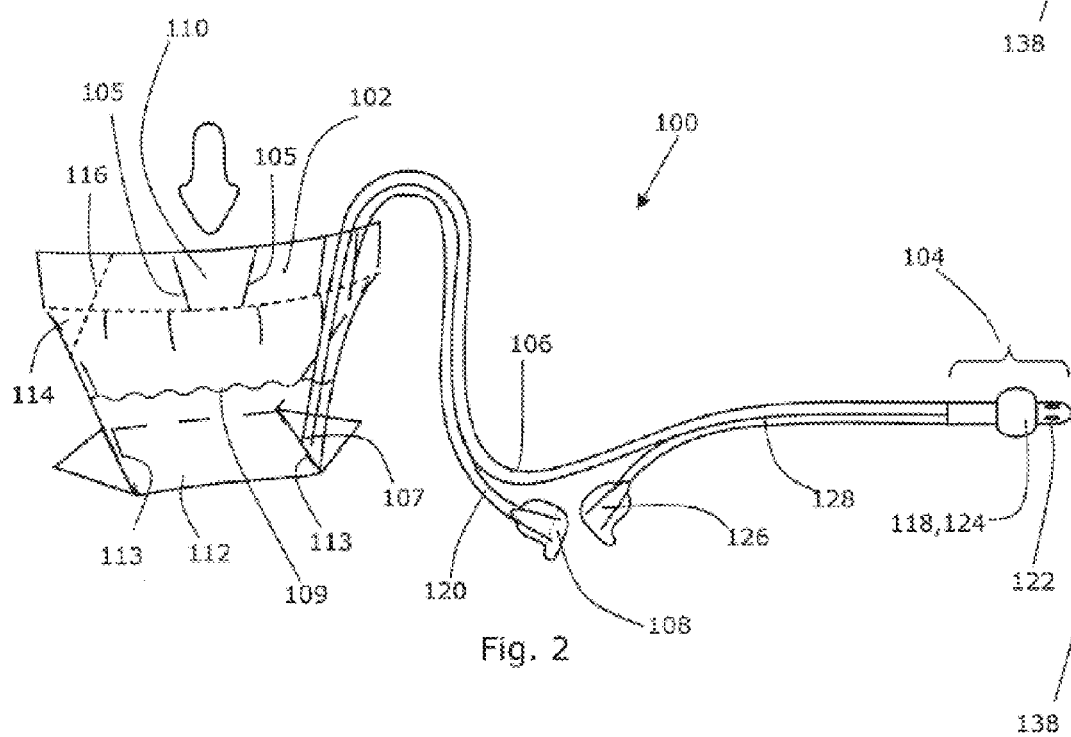

The embodiment of FIG. 2 differs from that of FIG. 1 in that the retaining means 118 is provided in the form of an inflatable balloon 124. In order to inflate the balloon, the irrigation system 100 also comprises a balloon pump 126 connected to the inflatable balloon 124 via a balloon tube 128. The balloon tube 128 may be permanently fastened to at least one of the inflatable balloon 124 and the balloon pump 128. It will be appreciated that the balloon pump 126 may comprise a non-return valve as described in relation to the gas pump 108.

In the embodiments of FIGS. 1 and 2 at least a part of the liquid tube 106 and the gas tube 120 are attached to each other. In one embodiment the two tubes define a monolithic element i.e. defining one element without seams. In the embodiment of FIG. 2 the liquid tube 106 and the balloon tube 128 are also attached to each other.

Figure 3:
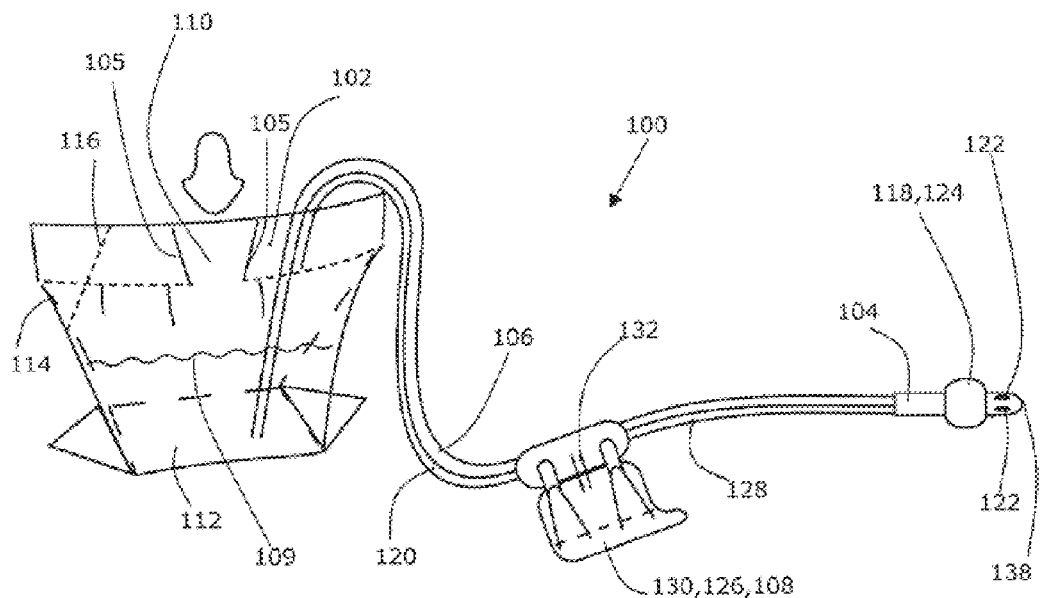

FIG. 3 discloses an alternative to the embodiment of FIG. 2. In FIG. 3 the balloon pump 126 and the gas pump 108 are integrated into one single unit defining a switchable pump 130. Moreover, the switchable pump 130 may be an individually positionable pump adapted to be positioned at any position along the liquid tube 106 thus allowing the user to position the pump 130 at a preferred position. Thus, the positionable pump may for example also be placed on the balloon tube 128, or alternatively on the gas tube 120.

The switchable pump 130 comprises a switch 132 allowing the user to change between inflation of the reservoir 102 and the inflatable balloon 124. The switch 132 is changeable between a first position wherein the switchable pump 130 is in fluid connection with the reservoir 102 and a second position wherein the switchable pump 130 is in fluid connection with the inflatable balloon 124. When switch 132 is positioned in the first position the switch is adapted to prevent deflation of the inflatable balloon 124 and when positioned in the second position the switch 132 is adapted to prevent deflation of the reservoir 102.

In the embodiment of FIG. 3, the switchable pump 130 defines two hollow piercing members (not shown)—one for cutting through the gas tube inlet 120 and one for cutting through the balloon tube 128, so as to fluidly connect the pump 130 to said tubes. Moreover, as the balloon tube 128 and the gas tube 120 initially are defined by the same tube, the pump 130 comprises means (not shown) for preventing fluid connection between the two tubes 120,128. Such means are positioned between the two piercing members. The hollow piercing members are described in further detail in relation to FIG. 9.

Figure 4:
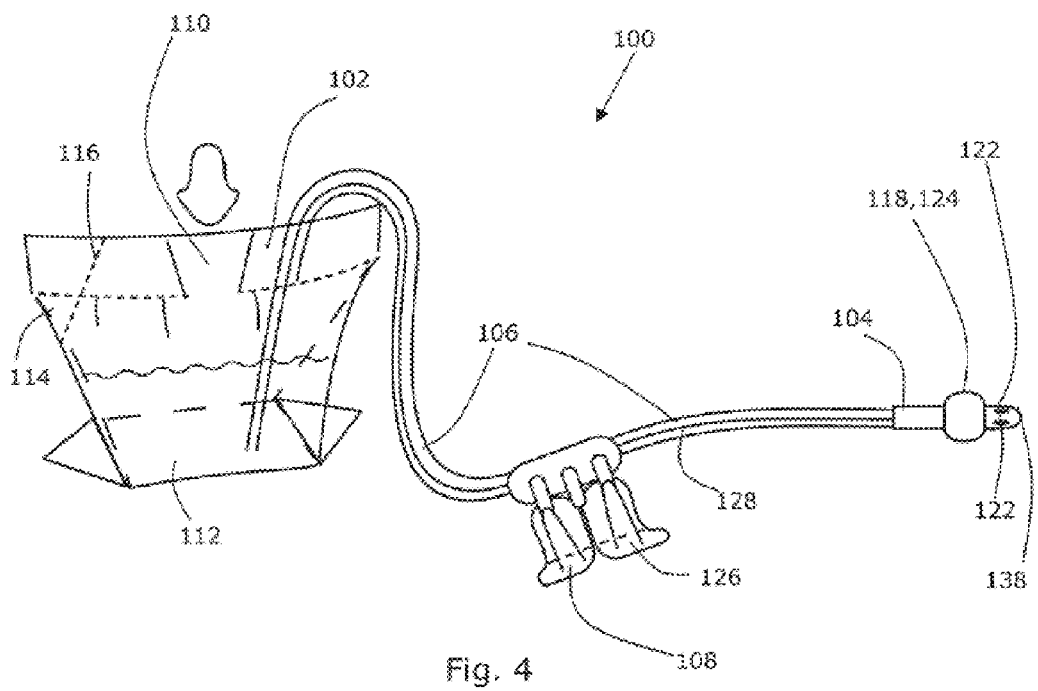

The embodiment of FIG. 4 differs from that of FIG. 3 in that the gas pump 108 and the balloon pump 126 are provided as two separate devices attached to each other, whereby the switch 132 of FIG. 3 is eliminated. The method of attaching the pumps 108,126 to the tubes 120,128, is similar to the method of attachment described in relation to FIG. 3.

The system of FIG. 5 differs from that of FIG. 2 in that the pump device 6 is an in-line sealed pump device e.g. as the one illustrated in FIG. 7. Alternatively, the pump is an individually positionable pump device as illustrated in FIG. 9. The liquid tube 106 and the gas tube 120 are provided in form of a double lumen tube permanently fastened to the reservoir 102 and the insertion member 104.

FIG. 6 discloses the insertion member 104. The insertion member 104 defines two coextending conduits—a balloon conduit 134 and a liquid conduit 136. In use the balloon conduit 134 is in fluid connection with the balloon tube 128 and the liquid conduit 136 is in fluid connection with the liquid tube 106. The insertion member 104 defines one or more openings 122 at its proximal end 138. During irrigation water displaced from the reservoir 102 is expelled through the at least one opening 122 and into the body cavity of the user. The proximal end 138 defines a smooth surface adapted to reduce discomfort during insertion into the body cavity through the body opening such as a natural/artificial anus of the user. Moreover, the insertion member 104 may comprise an indicator (not shown) for indicating how far into the body cavity the insertion member 104 should be inserted during irrigation. As an example the insertion member 104 must in some embodiments be inserted such that the indicator and the anus are aligned. The inflatable balloon 124 is adapted to be filed with gas in the range of 100-300 ml, though other sizes may be used depending on the user and the balloon length. The balloon can be made of an elastic material such as PUR, SEBS, Silicone, cloropen, nitril or nature latex, alternative the balloon can be made of a non-elastic material like Nylon, polyester, PP or PE.

FIG. 7 discloses the intestinal irrigation system 100 in a compacted state in which it is delivered to the user. In said compacted state, the tubes 137, the inserting member 104 and the pump 135 are wrapped around the reservoir 102 so as to provide the compact configuration. In other embodiments, said elements are provided in a folded state on top of the folded reservoir.

Figure 8A:
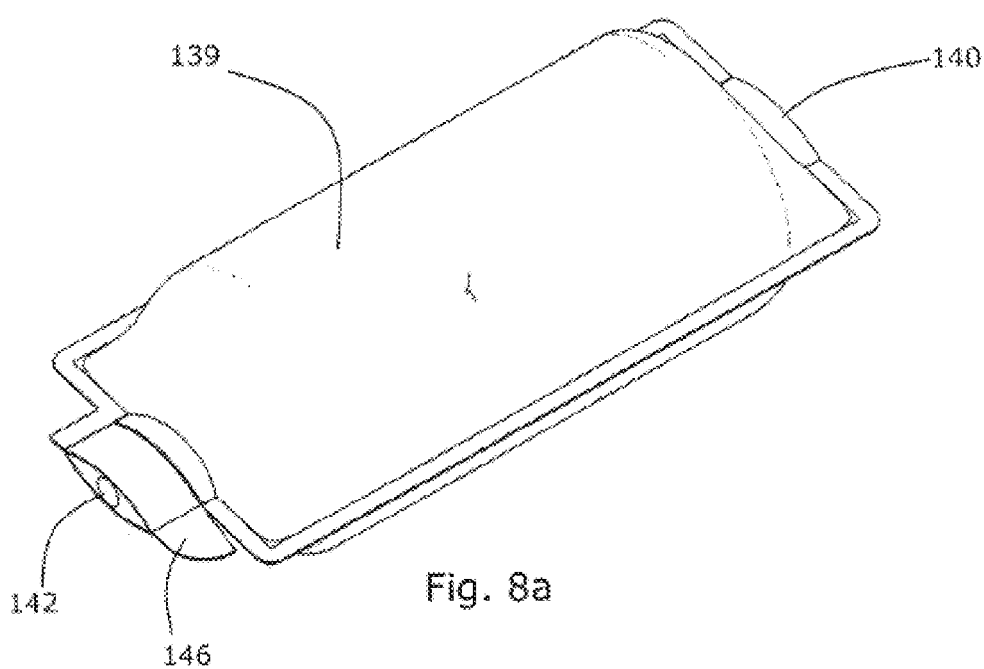
Figure 8B:
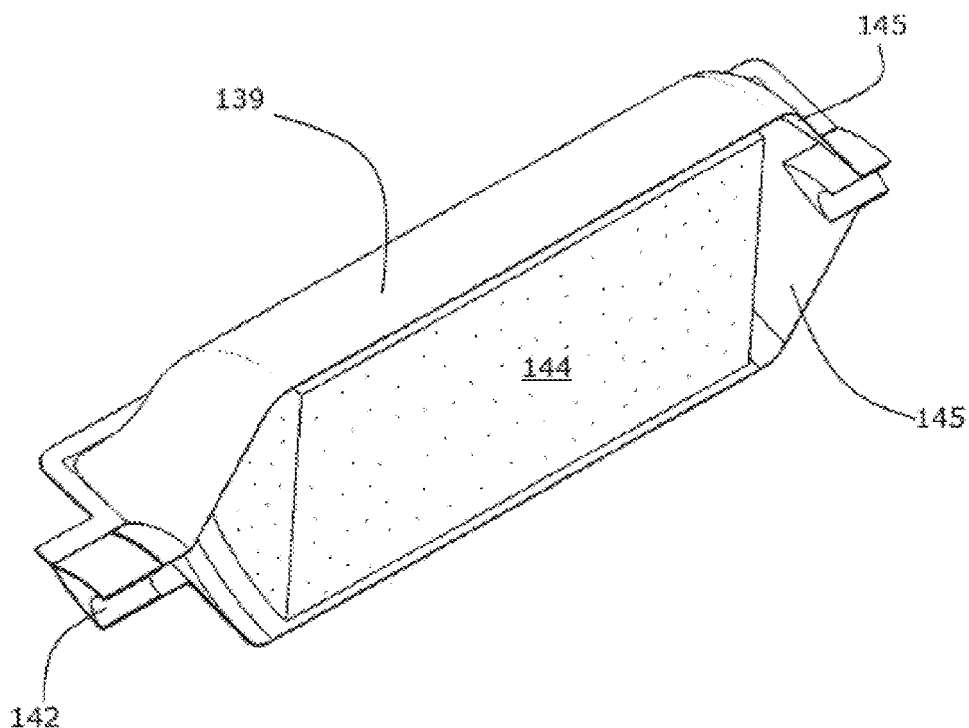

FIGS. 8a and 8b disclose an embodiment of the aforementioned foil pump 139 which defines a gas inlet 140 comprising a non-return valve (not shown) which may be manufactured in the same way as the foil pumps disclosed in WO2005/048890 i.e. only allowing air into the foil pump 139 and preventing air from escaping the foil pump 139 through the gas inlet 140. Moreover, the foil pump 139 defines a gas outlet 142 pump. The foil pump 139 comprises an open-celled foam 144 visible in FIG. 8b, which is surrounded by a foil 145. The foil pump 139 comprises a pump leaf 146 which when torn off enables the user to deflate the reservoir after irrigation and in order to discretely dispose the system in a bin or a container.

FIGS. 9a-9f disclose an individually positionable pump 148 adapted to be attached to the liquid tube 106 and the gas tube 120 by the user at any position of the tubes in accordance with the preferences of the user. In FIG. 9a and FIG. 9b the individually positionable pump 148 is shown in an open configuration allowing the liquid tube 106 to be positioned in first depressions 150. Moreover, the positionable pump 148 defines second depressions 152 for receiving the gas tube 120 as is describe in further detail below. The individually positionable pump 148 comprises an upper part 154 and a lower part 156 which are hinged together through hinge 158. The upper part 154 defines a snap projection 160 adapted to be received in a snap indentation 162 of the lower part 156 so as to snap-lock the upper part 154 to the lower part 156. Moreover, each of the upper and lower part 154,156 comprises a first depression 150 and a second depression 152.

The positionable pump 148 may comprise a resilient, open celled, foam 144 enclosed in a foil 145. The foil 145 may be a plastic foil made of a thermoplastic elastomer like Styrol-Block-Copolymere such as SEBS or PUR or a thermoplast like Polypropylen (PP), PE and PVC.

In order to fluidly connect the positionable pump 148 with the gas tube 120, the positionable pump 148 comprises a cannula 164 with a cutting edge, which during snapping of the upper part 154 to the lower part 156 penetrates the gas tube 120.

FIG. 9f discloses the positionable pump 130 in a closed state wherein the upper part 154 is snap-locked to the lower part 156 such that the cannula 164 penetrates the gas tube 120. Accordingly, by compressing foam 144 at least a part of the gas contained in the foam 144 is displaced into the gas tube 120 through the cannula 164. In order to allow the foam to expand and be refilled with gas (air) the foam 144 may define a plurality of openings which during compression are covered by the hand of the user compressing the foam, but which when the hand is removed allows the foam to be refilled. Moreover, the positionable pump 130 may comprise a non-return valve preventing gas/air to be sucked out of the gas tube 120 when the user removes his hand.

FIG. 10 discloses yet another embodiment of a disposable intestinal irrigation system, which differs from the system of FIG. 5 in that in that a liquid contained in the reservoir 102 is expelled through the opening 122 of the insertion member 104 by means of an inline pump 166. Accordingly, in FIG. 10 the liquid is not displaced from the reservoir 102 by increasing the pressure inside the reservoir 102 but by sucking the liquid out of the reservoir 102 by means of the inline pump 166. The inline pump 166 comprises a non-return valve preventing liquid downstream the pump from flowing upstream relative the inline pump 166. Accordingly, upon compression of the inline pump 166 the liquid contained in the pump is forced to flow downstream and upon decompression of the inline pump 166 liquid downstream the pump is sucked into the chamber of the inline pump 166. The inline pump 166 may comprise a resilient material as described in the aforementioned. A further difference between FIGS. 10 and 5 is that the retaining means 118 of FIG. 10 is a cone-shaped as described in relation to FIG. 1.

FIGS. 11a and 11b discloses a part of a reservoir 102 of an irrigation system. For simplicity reasons only the lower part of the reservoir 102 is disclosed in FIG 11a. However, it will be appreciated that the reservoir 102 of FIG. 11a may also comprise an inlet, which is closable as is described in the aforementioned. A cross-section of the reservoir 102 is disclosed in FIG. 11b. The reservoir 102 comprises three sheets of foil 168,170,172 one of which defines a membrane 172 dividing the reservoir 102 into a gas chamber 174 and liquid chamber 176. The three sheets of foil 168,170,172 are attached to each other along the rim 178, e.g. by means of welding. During use, the user fills water into the liquid chamber 176 and closes the inlet (not shown). Subsequently the user pressurises the gas chamber 174, e.g. by means of one of the aforementioned pumps. This causes the gas chamber 174 to expand whereby the volume of the liquid chamber 176 decreases and any liquid contained in the liquid chamber 176 is displaced into the liquid tube 106. An increase in volume of the gas chamber 174 is disclosed in FIG. 11b wherein the line 172 illustrates a position of the membrane prior to inflation of the gas chamber 174 and the dotted-line 172' illustrates a position of the membrane when the gas chamber 174 is pressurised.

Figure 12:
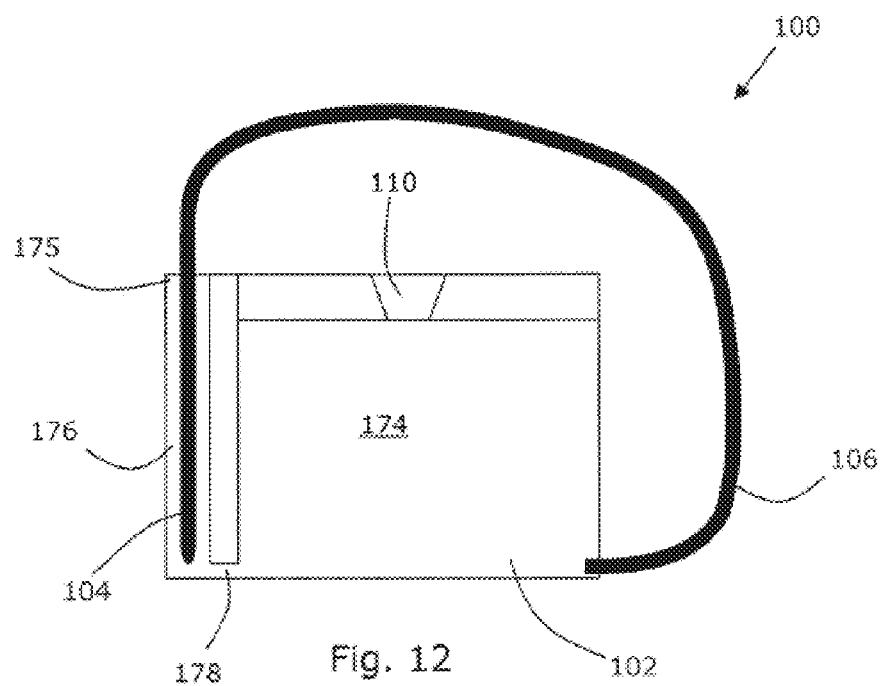

FIG. 12 discloses an irrigation system 100 wherein the inserting member 104 is provided in the reservoir 102 on delivery. The reservoir 102 defines a compression compartment 174 adapted to be pressurised so as to allow liquid contained in the compartment 174 to be displaced into the liquid tube 106. Moreover, the reservoir 102 defines a swelling compartment 176 adapted to accommodate the inserting member 104. The swelling compartment 176 and the compression compartment 174 are fluidly connected via a passage 178. When the irrigation system 100 is delivered to the user, the inserting end 104 is provided in the swelling compartment 176 and in order to initiate the swelling process, the user must fill a liquid such as water into the compression compartment 174 via the inlet 110. Due to the passage 178 the liquid flows from the compression compartment 174 into the swelling compartment 176, whereby a hydrophilic coating on the outer surface of the inserting member 104 is subjected to the swelling medium (the liquid). After a predetermined period of time, the user may remove the inserting member 104 from the swelling compartment 176 and insert the inserting member 104 into the body cavity. In one embodiment, the passage 178 is designed such that upon removal of the inserting member 104 the passage is closed whereby pressurisation of the compression compartment 174 does not cause the liquid to be displaced into the swelling compartment 176. In one embodiment the passage comprises an non-return valve such as the one disclosed in U.S. Pat. No. 4,581,763. In another embodiment the user must close the passage manually. When the passage is closed, the compression compartment may be pressurised, whereby any liquid contained in the compartment is displaced into the liquid tube 106 as is described in the aforementioned.

Figure 13:
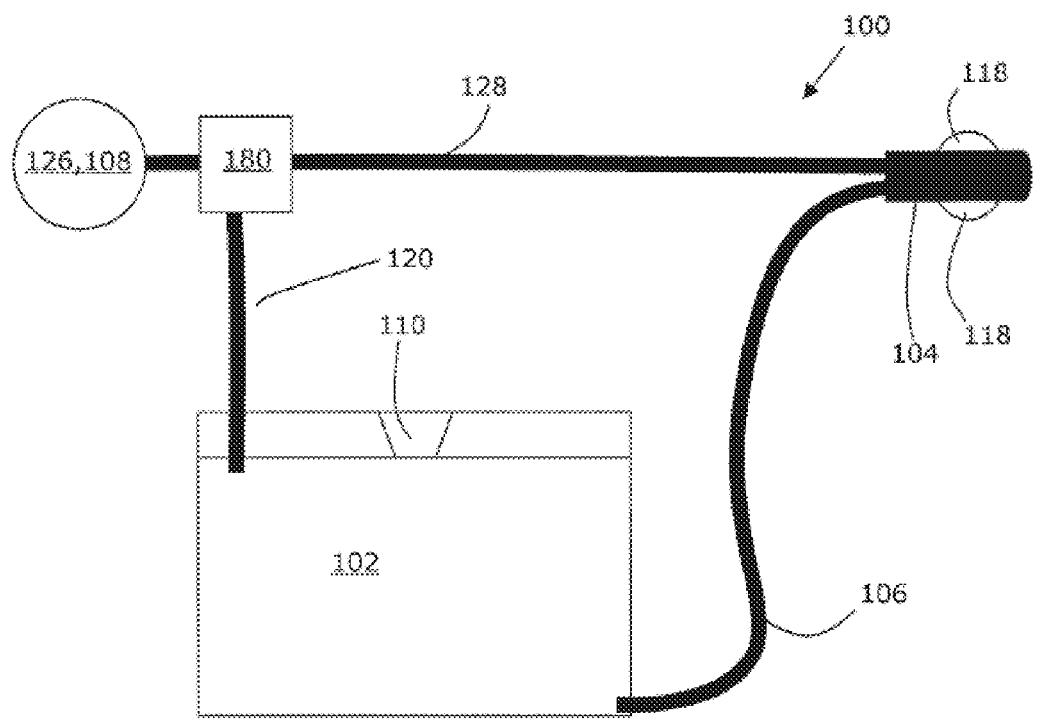

FIG. 13 discloses an irrigation system 100 comprising a reservoir 102 connected to an inserting member 104 via a liquid tube 106. The inserting member 104 comprises a retaining means 118 in the form of a balloon, which may be inflated by means of a balloon pump 126, which is connected to the balloon via a balloon tube 128. The balloon tube 128 comprises an over-pressure valve 180, which is adapted to open when the pressure in the valve 180 is above a predetermined level whereby gas is guided into the reservoir 102 via the gas tube 120. Accordingly, the balloon pump 126 also serves as a gas pump 108.

During use the user fills water into the reservoir 102 through the opening 110 and inserts the inserting member 104 into the body cavity. Subsequently, the user operates the pump 108,126 whereby the balloon is inflated and the inserting member 104 is retained in the body cavity. When the pressure exceeds a predetermined pressure level, air is guided into the reservoir 102 which is then inflated. The inflation process causes any liquid contained in the reservoir 102 to be displaced into the liquid tube 106 and out through the inserting member 104.

FIGS. 14a and 14b discloses an automatic valve 200 for use in the embodiment described with respect to FIG. 3, where the switch 132 is replaced with the current automatic valve and with respect to FIG. 13, where the automatic valve is used as the over-pressure valve 180.

The automatic valve is formed with a valve housing 201 enclosing a piston chamber 202 wherein a piston 203 is slidably arranged. The piston is formed with a first and a second piston head 204,205 separated by a shaft 206.

An inlet channel 207 is provided allowing for fluid communication into the chamber 202.

Similarly there is provided a first and second outlet channel 208,209. A spring 210 is provided in the end of the piston chamber closest to the first outlet channel 208. The spring is dimensioned so that it biases the piston into a first position shown in FIG. 14A where the first piston head 204 blocks for passage to the first outlet channel 208 but allows for fluid communication from the inlet channel to the second outlet channel 209 between the two piston heads. A pressure channel 211 is provided in communication with the second outlet channel 209 and a pressure chamber 212 which is provided in a section of the piston chamber defined by the second piston head 205 and the end wall of the piston chamber opposite the spring.

When using the valve together with embodiment disclosed in FIG. 13, i.e. as the over-pressure valve 180 the inlet channel 207 is connected with the pump 108,126, the first outlet channel 208 is connected with the gas tube 120 and the second outlet channel 209 is connected with the balloon tube 128.

As pumping is initiated gas will be pumped from the inlet channel and out through the second outlet channel and into the balloon via the balloon tube. As pressure builds in the balloon the same pressure will build up in the pressure chamber 212. By dimensioning the spring 210 properly it can be set to compress when the pressure in the balloon (and also the pressure chamber) reaches a predetermined level. As the spring compress the piston shifts into a second position shown in FIG. 14B where the second piston head closes off the second outlet channel and the first outlet channel is exposed as the first piston head is moved away. This provides for fluid communication from the inlet channel to first outlet channel and into the reservoir via the gas tube 120.

As can be understood the first inlet channel should be arranged between the first and second outlet channel when looking along the displacement axis of the piston in such a way that neither of the piston heads covers the inlet channel in the first or second position of the piston.

Figure 15:
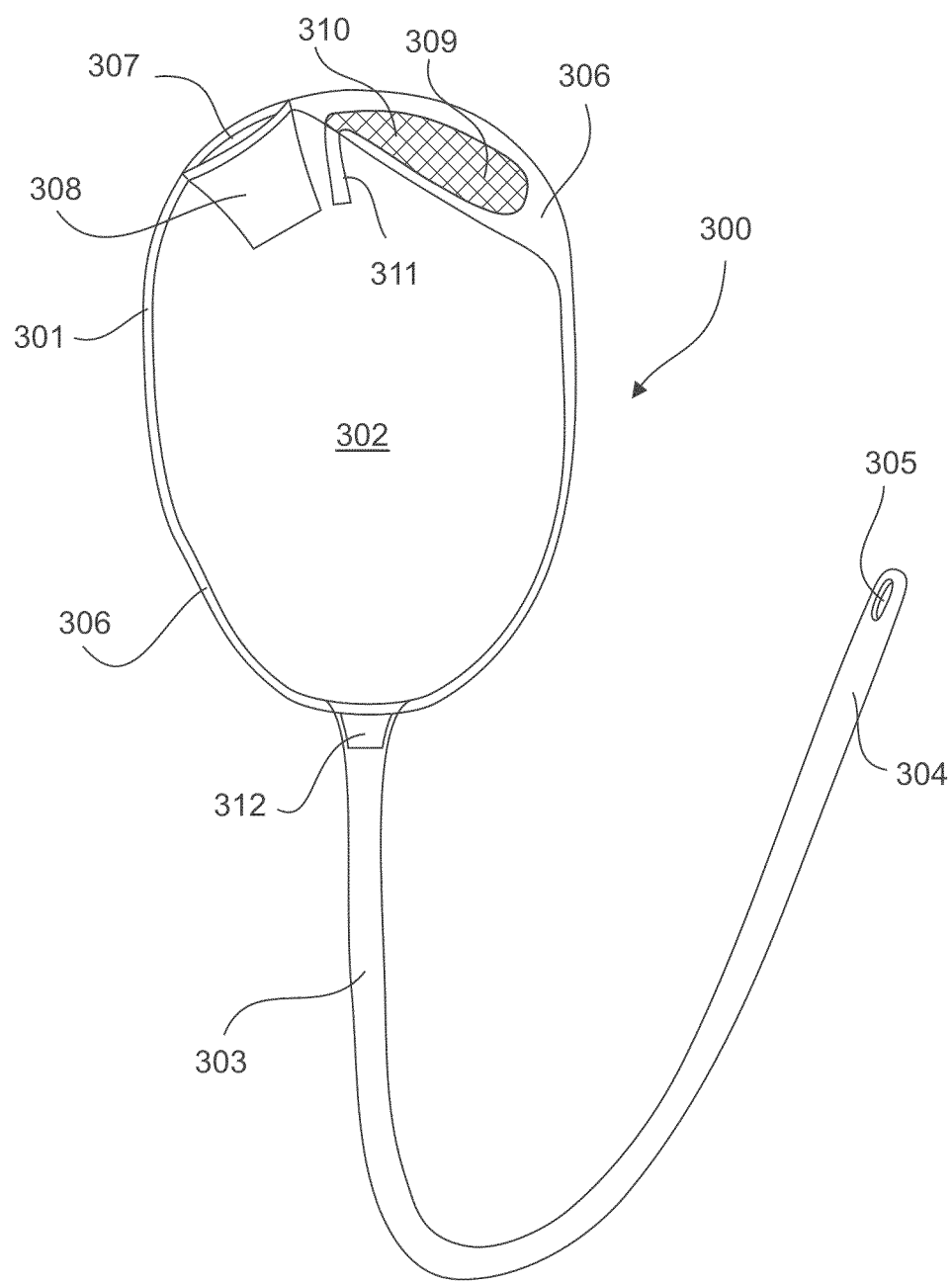

FIG. 15 shows an embodiment of an irrigation system 300 comprising a reservoir bag 301 defining a reservoir 302 and a liquid tube 303 communicating with the reservoir 302. The liquid tube extends into an insertion member 304, e.g. in the form of a rectal catheter/probe having at least one eyelet 305 through which irrigation fluid may be evacuated. Although not shown the insertion member 304 may be provided with retention means, e.g. a conus or inflatable balloon as described previously, which serves to retain the insertion member in the rectum while irrigation is performed.

The reservoir bag 301 is formed of two plastic sheets welded together along a weld 306. The liquid tube is connected to a first half of the reservoir bag, and in an opposite second half of the reservoir bag there is provided an opening 307. The opening allows the reservoir to be filled with irrigation fluid. The opening is provided with a one-way foil valve 308, which allows liquid to be easily poured into the reservoir but prevents it from running back out. Such foil valves are well known in the art.

When manufacturing the reservoir bag, i.e. the two foil sheets are welded together a second chamber 309 is provided by welding around an area of the foil sheets. In the second chamber there is provided a resilient element 310, e.g. in the form of a foam. The second chamber communicates with the outside of the bag via a non-return valve (not shown) allowing gas (typically air) to enter the second chamber but not flow back out. Furthermore, the second chamber communicates with the reservoir via a second one-way foil valve 311, allowing gas to enter the reservoir from the second chamber but not flow the other way. One-way valves are well known in the art, and the skilled person would not have any difficulty finding valves, which are well suited for the present embodiment.

Thus, as the second chamber is compressed it will force air into the reservoir and subsequently when the second chamber is released it will expand due to the resilient element and air will be sucked into the second compartment. This compression and release is repeated, generating a pumping action, which generates a pressure in the reservoir forcing irrigation liquid from the reservoir out into the liquid tube and through the eyelet.

Furthermore, a biased valve 312 can be provided in the liquid tube. The biased valve prevents fluid to flow from the reservoir and through the liquid tube until a predetermined pressure has been built within the reservoir. This prevents that the irrigation system drips unintentionally. Furthermore, in order to prevent backflow and avoid content of the bowels to flow through the liquid tube and into the reservoir the biased valve is designed so to prevent flow in this direction.

As can be understood the embodiment disclosed in FIG. 15 may be easily manufactured as the entire reservoir bag including pump may be produced in one welding step The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An irrigation system for irrigation of a body cavity, the system comprising:
 a reservoir with an inlet for pouring liquid into the reservoir, the inlet defining a closing element for closing the inlet;
 an insertion member defining an insertion end adapted to be inserted into a body cavity through a body opening of a human being, the insertion member defining at least one opening;
 a liquid tube fluidly connecting the reservoir with the insertion member,
 with both the reservoir and the insertion member being permanently fastened to the liquid tube;
 a pump for pumping liquid from the reservoir and out through the at least one opening of the insertion member;
 wherein the pump is a manual pump being a foil pump with a resilient element;
 wherein the resilient element includes an open-celled foam.

2. The irrigation system according to claim 1, wherein the pump is an electrical pump.

3. The irrigation system according to claim 2, wherein the electrical pump includes a manually operable generator including a crank which when operated causes the generator to charge a rechargeable battery of the electric pump.

4. The irrigation system according to claim 1, wherein the pump is a peristaltic pump.

5. The irrigation system according to claim 1, wherein the liquid tube is a foil tube.

6. The irrigation system according to claim 1, wherein the pump is a liquid pump with a pump inlet and a pump outlet, the pump inlet and the pump outlet being permanently fastened to the tube, such that operation of the pump causes a liquid contained in the reservoir to flow out through the at least one opening of the insertion member.

7. The irrigation system according to claim 2, wherein the electrical pump includes a control unit for controlling liquid flow in the system.

8. The irrigation system according to claim 7, wherein the control unit is adapted to change a rate of the liquid flow in a predetermined sequence.

9. The irrigation system according to claim 1, wherein the pump is a gas pump arranged relative to the reservoir that upon activation of the pump, gas pressure in the reservoir increases whereby a liquid contained in the reservoir flows into the liquid tube and out through the at least one opening.

10. The irrigation system according to claim 9, further comprising a gas tube fluidly interconnecting the gas pump and the reservoir.

11. The irrigation system according to claim 10, wherein the gas tube is a foil tube.

12. The irrigation system according to claim 10, wherein the gas tube is permanently fastened to one of the the gas pump and the reservoir.

13. The irrigation system according to claim 1, wherein the insertion member includes a retaining element for retaining the insertion member in the body cavity when inserted through the body opening.

14. The irrigation system according to claim 13, wherein the retaining element includes a balloon fluidly connected with a balloon pump such that operation of the balloon pump causes the balloon to expand.

15. The irrigation system according to claim 14, wherein the balloon is selected from the group consisting of a gas balloon and a liquid balloon.

16. The irrigation system according to claim 1, further comprising a switchable pump, the switchable pump being configured as (i) a gas pump arranged relative to the reservoir such that upon activation of the pump, gas pressure in the reservoir increases whereby a liquid contained in the reservoir flows into the liquid tube and out through the at least one opening and (ii) a balloon pump that inflates a gas balloon associated with the insertion member, the switchable pump having a switch defining a first position in which the switchable pump is fluidly connected to the gas balloon, and a second position in which the switchable pump is fluidly connected to the reservoir.

17. The irrigation system according to claim 13, wherein the retaining element is defined on an outer surface of the insertion member.

* * * * *